(12) United States Patent
Gorek

(10) Patent No.: US 8,414,625 B2
(45) Date of Patent: *Apr. 9, 2013

(54) MINIMALLY INVASIVE RETRACTION DEVICE HAVING REMOVABLE BLADES

(75) Inventor: Josef Gorek, Ross, CA (US)

(73) Assignee: K2M, Inc., Leesburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/333,496

(22) Filed: Dec. 21, 2011

(65) Prior Publication Data

US 2012/0116460 A1    May 10, 2012

Related U.S. Application Data

(63) Continuation of application No. 12/396,188, filed on Mar. 2, 2009, now Pat. No. 8,097,026.

(60) Provisional application No. 61/032,135, filed on Feb. 28, 2008.

(51) Int. Cl.
    *A61B 17/88* (2006.01)

(52) U.S. Cl.
    USPC .......................... 606/279; 606/305; 606/304

(58) Field of Classification Search ........... 606/304–306, 606/308, 279, 104, 86 A, 99; 600/214, 219, 600/206, 235; 264/259; 156/60; 81/460, 81/461

See application file for complete search history.

(56) References Cited

U.S. PATENT DOCUMENTS

| | | | |
|---|---|---|---|
| 3,129,706 A | 4/1964 | Reynolds | |
| 3,486,505 A | 12/1969 | Morrison | |
| 5,242,443 A | 9/1993 | Kambin | |
| 5,431,658 A | 7/1995 | Moskovich | |
| 5,496,321 A | 3/1996 | Puno | |
| 5,545,165 A | 8/1996 | Biedermann | |
| 5,582,577 A | 12/1996 | Lund | |
| 5,685,826 A | 11/1997 | Bonutti | |
| 5,797,911 A | 8/1998 | Sherman | |
| 5,902,231 A | 5/1999 | Foley et al. | |
| 5,944,658 A | 8/1999 | Koros et al. | |
| 6,063,088 A | 5/2000 | Winslow | |
| 6,083,225 A | 7/2000 | Winslow et al. | |
| 6,099,547 A | 8/2000 | Gellman et al. | |
| 6,102,951 A | 8/2000 | Sutter | |
| 6,146,385 A | 11/2000 | Torrie et al. | |
| 6,187,000 B1 | 2/2001 | Davison et al. | |
| 6,200,322 B1 | 3/2001 | Branch et al. | |
| 6,206,826 B1 | 3/2001 | Mathews et al. | |
| 6,270,501 B1 | 8/2001 | Freiberg et al. | |
| 6,280,442 B1 | 8/2001 | Barker | |
| 6,358,253 B1 | 3/2002 | Torrie et al. | |
| 6,360,750 B1 | 3/2002 | Gerber et al. | |

(Continued)

FOREIGN PATENT DOCUMENTS

WO    WO 2007/084641    7/2007

*Primary Examiner* — Pedro Philogene

(74) *Attorney, Agent, or Firm* — Carter, DeLuca, Farrell & Schmidt, LLP

(57) ABSTRACT

A retraction device comprises at least one retracting blade and a pedicle screw. The retracting blade has a distal end having at least one projection with a passage for engaging a retention pin. The pedicle screw has a threaded body and a movable head. The movable head has at least one recess with a channel that can be aligned with the passage of the projection.

14 Claims, 6 Drawing Sheets

U.S. PATENT DOCUMENTS

| | | |
|---|---|---|
| 6,478,800 B1 | 11/2002 | Fraser et al. |
| 6,485,494 B1 | 11/2002 | Haider |
| 6,530,926 B1 | 3/2003 | Davison |
| 6,530,929 B1 | 3/2003 | Justis et al. |
| 6,616,605 B2 | 9/2003 | Wright et al. |
| 6,652,533 B2 | 11/2003 | O'neil |
| 6,669,729 B2 | 12/2003 | Chin |
| 6,740,091 B2 | 5/2004 | Kohrs et al. |
| 6,743,206 B1 | 6/2004 | Smith |
| 6,755,841 B2 | 6/2004 | Fraser et al. |
| 6,796,422 B1 | 9/2004 | Lu |
| 6,800,084 B2 | 10/2004 | Davison et al. |
| 6,849,064 B2 | 2/2005 | Hamada |
| 6,929,606 B2 | 8/2005 | Ritland |
| 7,008,422 B2 | 3/2006 | Foley et al. |
| 7,011,660 B2 | 3/2006 | Sherman et al. |
| 7,056,321 B2 | 6/2006 | Pagliuca et al. |
| 7,083,621 B2 | 8/2006 | Shaolian et al. |
| 7,108,705 B2 | 9/2006 | Davison et al. |
| 7,144,393 B2 | 12/2006 | Dipoto et al. |
| 7,160,300 B2 | 1/2007 | Jackson |
| 7,166,107 B2 | 1/2007 | Anderson |
| 7,179,261 B2 | 2/2007 | Sicvol et al. |
| 7,188,626 B2 | 3/2007 | Foley et al. |
| 7,250,052 B2 * | 7/2007 | Landry et al. ............... 606/86 A |
| 7,491,208 B2 * | 2/2009 | Pond et al. ................... 606/104 |
| 8,097,026 B2 * | 1/2012 | Gorek .......................... 606/279 |
| 2003/0004401 A1 | 1/2003 | Ball |
| 2003/0191371 A1 | 10/2003 | Smith |
| 2004/0138662 A1 | 7/2004 | Landry et al. |
| 2004/0143265 A1 | 7/2004 | Landry et al. |
| 2005/0065517 A1 | 3/2005 | Chin |
| 2005/0131408 A1 | 6/2005 | Sicvol et al. |
| 2005/0131421 A1 | 6/2005 | Anderson et al. |
| 2005/0154389 A1 | 7/2005 | Selover et al. |
| 2005/0165408 A1 | 7/2005 | Puno et al. |
| 2005/0215999 A1 | 9/2005 | Birkmeyer et al. |
| 2006/0074445 A1 | 4/2006 | Gerber et al. |
| 2006/0200135 A1 | 9/2006 | Sherman et al. |
| 2006/0229614 A1 | 10/2006 | Foley et al. |
| 2006/0264962 A1 | 11/2006 | Chin et al. |
| 2007/0049931 A1 | 3/2007 | Justis et al. |
| 2007/0055247 A1 | 3/2007 | Jahng |
| 2007/0106123 A1 | 5/2007 | Gorek |
| 2007/0129731 A1 | 6/2007 | Sicvol et al. |
| 2007/0167954 A1 | 7/2007 | Sicvol et al. |
| 2008/0114403 A1 | 5/2008 | Kuester et al. |
| 2008/0119849 A1 | 5/2008 | Beardsley et al. |
| 2009/0131755 A1 * | 5/2009 | White et al. ................... 600/210 |
| 2009/0221877 A1 | 9/2009 | Woods |
| 2009/0221879 A1 | 9/2009 | Gorek |
| 2009/0222044 A1 | 9/2009 | Gorek |
| 2009/0222045 A1 | 9/2009 | Gorek |
| 2011/0054259 A1 | 3/2011 | Gorek et al. |

* cited by examiner

MINIMALLY INVASIVE RETRACTION DEVICE HAVING REMOVABLE BLADES

CROSS-REFERENCE TO RELATED APPLICATIONS

This application is a continuation of U.S. patent application Ser. No. 12/396,188 filed Mar. 2, 2009, which claims priority to, and the benefit of, U.S. Provisional Patent Application No. 61/032,135, filed Feb. 28, 2008, the entire content of each of which are incorporated by reference herein.

BACKGROUND

1. Technical Field

The present disclosure relates generally to orthopedic spine surgery and in particular to devices, systems and methods for a pedicle screw-based retractor to be used in a minimally invasive surgical approach.

2. Background of the Technology

There has been considerable development of retractors and retractor systems that are adapted for use in less invasive procedures. Many of the recent developments are based on traditional types of surgical retractors for open procedures, predominantly table-mounted devices of various designs. These devices tend to be cumbersome and are not well adapted for use in small incisions. Standard hand-held surgical retractors are well known in the prior art and can be modified to fit the contours of these small incisions, but they require manual manipulation to maintain a desired placement, thereby occupying one hand of the physician or requiring another person to assist the physician during the procedure. Typical retractors are also positioned into the soft tissue and are levered back to hold the wound open, frequently requiring re-positioning if they dislodge, obstruct the physician's view, or interfere with access to the surgical site.

In recent years, minimally invasive surgical approaches have been applied to orthopedic surgery and more recently to spine surgery, such as instrumented fusions involving one or more vertebral bodies. Unlike minimally invasive procedures such as arthroscopic knee surgery or gallbladder surgery where the affected area is contained within a small region of the body, spinal fusion surgery typically encompasses a considerably larger region of the patient's body. In addition, arthroscopic surgery and laparoscopic surgery permit the introduction of fluid (i.e. liquid or gas) for distending tissue and creating working space for the surgeon. Surgery on the spine does not involve a capsule or space that can be so distended, instead involving multiple layers of soft tissue, bone, ligaments, and nerves. For these reasons, the idea of performing a minimally invasive procedure on the spine has only recently been approached.

By way of example, in a typical spine fusion at least two vertebral bodies are rigidly connected using screws implanted into the respective vertebral bodies with a solid metal rod spanning the distance between the screws. This procedure is not generally conducive to a minimally invasive approach. The insertion of pedicle or facet screws is relatively straightforward and can be accomplished through a minimal incision. The difficulty arises upon the introduction of a length of rod into a very small incision with extremely limited access and visibility. A single level fusion may require a 30-40 mm rod to be introduced into a 1 cm incision and a multilevel fusion may require a rod several inches long to fit into a 1 cm incision. For this reason, it is important that the minimal incision be maintained in an open and accessible condition (i.e. as wide as practicable) for introduction of the rod.

Minimally invasive surgery offers significant advantages over conventional open surgery. First, the skin incision and subsequent scar are significantly smaller. By using more than one small incision rather than one large incision, the need for extensive tissue and muscle retraction may be greatly reduced. This leads to significantly reduced post-operative pain, a shorter hospital stay, and a faster overall recovery.

Most spine implant procedures are open procedures, and while many manufacturers advertise a minimally invasive method, the procedure is typically not recommended for fusions and focuses on more common and accepted minimally invasive spine procedures such as kyphoplasty, vertebroplasty, and discectomy.

Medtronic Sofamor Danek's SEXTANT® is a minimally invasive device used for screw and rod insertion. Its shortcomings lie with how complicated the system is to use and the requirement for an additional incision for rod introduction. This system also requires that the guidance devices be rigidly fixed to the pedicle screw head in order to maintain instrument alignment and to prevent cross-threading of the setscrew. For these reasons, the surgeon cannot access the surrounding anatomy for complete preparation of the field. Nor does SEXTANT® allow for any variation in the procedure, if need be.

Depuy Spine's VIPER™ system is another minimally invasive implant and technique recommended for one or two level spine fusions. This system is less complicated than the SEXTANT® only requiring two incisions for a unilateral, one-level fusion, but it is limited in the same way as the SEXTANT® because it also requires the instrumentation to be rigidly fixed to the pedicle screw.

Spinal Concept's PATHFINDER® and NuVasive's SPHERX® spinal system (as disclosed in U.S. Pat. No. 6,802,844), are marketed as "minimally disruptive" spine fusion implants and procedures. While they have advantages over a general "open" procedure, they do not provide all of the advantages of a truly minimally invasive approach. Their characterization as "minimally open" procedures is a result of the inherent difficulty of introducing a rod in a minimally invasive spinal procedure. In order to introduce a rod long enough to accomplish a single level fusion, these systems describe an incision long enough to accept such a rod, thereby undermining the advantages of a minimally invasive approach.

The problem of rod introduction warrants further discussion as it is the central problem in minimally invasive spinal fusions. The systems currently on the market address this issue by adding another incision, using a larger incision, or avoiding fusions greater than one level.

In order to be truly minimally invasive, a spine fusion procedure should have a minimum number of small incisions and not require significant tissue and/or muscle retraction. Furthermore, an improved approach should encompass as many variations and applications as possible thereby allowing the surgeon to adjust the procedure to accommodate the anatomy and surgical needs of the patient as presented. For instance, spinal fusions should not be limited to just one or two levels.

Therefore, a continuing need exists for an improved device, an improved system, and an improved method for performing minimally invasive spine surgery.

SUMMARY

The present disclosure is directed towards a retractor device, particularly a device used in spinal fusion surgery. The retractor device has at least one retracting blade and a pedicle screw. The retracting blade has a distal end having at least one projection with a passage therethrough. The pedicle screw has a threaded body and a movable head. The head has at least one retaining portion having at least one slot with a channel therethrough. The channel of the pedicle screw and the passage of the retracting blade align when the projection of the retracting blade is joined with the retaining portion of the pedicle screw. A retention pin may be used for releasably coupling the retraction blade and the pedicle screw by inserting it through the aligned passage of the retracting blade and the channel of the pedicle screw.

In one embodiment, the retractor device includes two retracting blades and a pedicle screw. Each retracting blade may have an arcuate shape and is configured for positioning about the head of the pedicle screw. The distal end of the retracting blades has a projection and a channel extending therethrough. The pedicle screw has a movable head that may be rotatable and/or have polyaxial articulation. The proximal end of the movable head has a retaining portion and a passage running therethrough. The retaining portion extends proximally from the movable head. It is contemplated that the retaining portion extends from the top of the head of the pedicle screw.

In a further embodiment, the retaining portion of the pedicle screw has a slot for receiving the projection of the retracting blade. As the projection of the retracting blade is inserted into the slot of the retaining portion, the passage of the retracting blade becomes aligned with the channel of the pedicle screw so that a retention pin may be placed therein. In other embodiments, the pedicle screw contains two retaining portions such that the projection of the retracting blade may be placed therebetween. The passage of the retracting blade aligns with the channels of the retaining portions of the pedicle screw so that a retention pin may be placed therein. Optionally, the retention pin may have a tether for ease of removal.

BRIEF DESCRIPTION OF THE DRAWINGS

Embodiments of the presently disclosed retractor device are disclosed herein with reference to the drawings wherein.

DETAILED DESCRIPTION OF THE EMBODIMENTS

Figure 1:
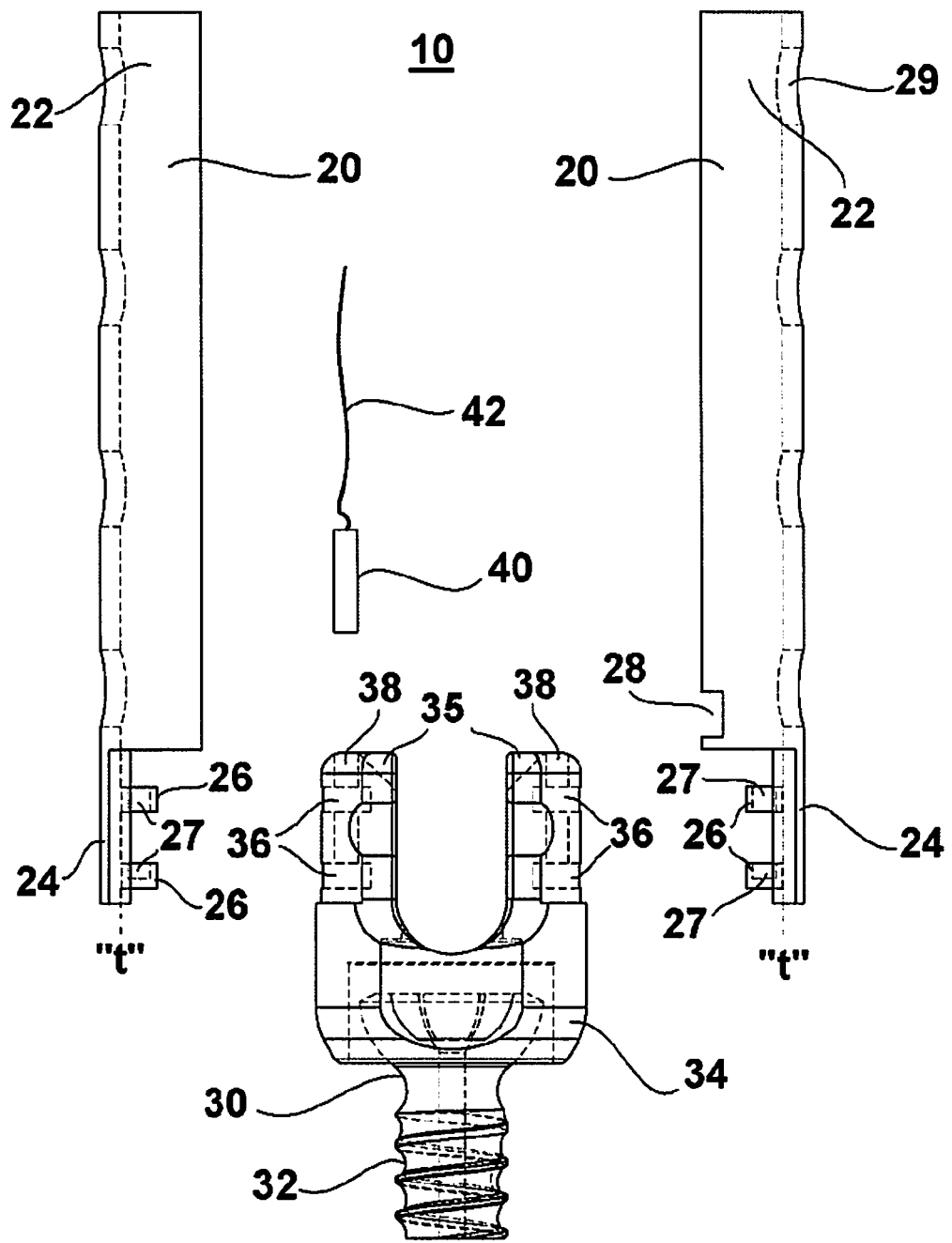
FIG. 1 is a side plan view of the retractor device, with parts separated, in accordance with the present disclosure.

The retractor device of the present disclosure is used to conduct minimally invasive spine surgery. A retracting blade is removeably attached to a pedicle bone screw which is used to guide the retractor into place and act as a point of fixation with respect to the patient. A retracting blade, pedicle bone screw, and systems and methods for use are disclosed in U.S. patent application Ser. No. 11/528,223 filed Sep. 26, 2006 (U.S. Patent Application Publication No. 2007/0106123), the entire contents of which are hereby incorporated by reference herein.

In the drawings and in the description that follows, the term "proximal," will refer to the end of a device or system that is closest to the operator, while the term "distal" will refer to the end of the device or system that is farthest from the operator.

Figure 2:
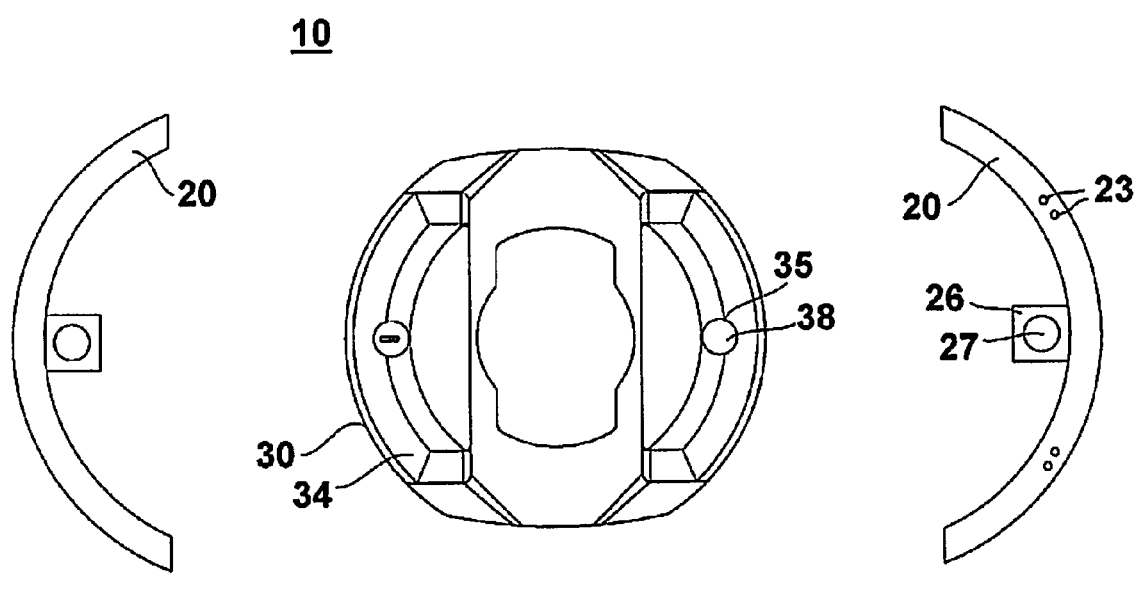
FIG. 2 is a top view of the retractor device of FIG. 1.

Referring now to the drawings, in which like reference numerals identify identical or substantially similar parts throughout the several views, FIGS. 1 and 2 illustrate a side plan view and a top view of the retractor device in accordance with the principles of the present disclosure. Retractor device 10 includes retracting blades 20 and pedicle screw 30. Pedicle screw 30 may be a monoaxial screw or may be a polyaxial screw, as shown. Retracting blades 20 are discussed singularly as they are substantially identical.

Retracting blade 20 includes proximal end 22 and distal end 24, and defines a longitudinal axis "t" extending along the length of the blade. Preferably, the cross-section of retracting blade 20, as clearly shown in FIG. 2, is generally a circular ring sector which provides stiffness to the retracting blade so that it will not yield to the counter force of the retracted tissue. Further, the arcuate or concave shape of retracting blade 20 is adapted and configured for positioning about pedicle screw 30 as well as for guiding insertion of other instruments.

Distal end 24 of retracting blade 20 includes at least one projection 26. Two projections 26 are illustrated in the current embodiment, each projection 26 being a substantially flat surface traverse to longitudinal axis "t". Each projection 26 includes passage 27 which is arranged coincident with longitudinal axis "t". Passage 27 may be circular, oval, oblong, square, rectangular, or other shape as known in the art.

Retracting blade 20 may include one or more living hinges 28 along proximal or distal ends 22, 24 so that retracting blade 20 may flex. The geometry is configured so that retracting blade 20 bends at living hinge(s) 28 and still is able to retract tissue against which it is pressed. More than one living hinge 28 may be incorporated to aid in bending along any portion of the blade's length. It is also contemplated that true hinges may be used in lieu of the disclosed living hinges 28.

Retracting blade 20 may also have one or more transverse through holes 29 disposed on the retractor at points along axis "t". When two or more retracting blades are used, standard surgical instruments, such as a Gelpi retractor, may be used to engage opposing holes 29 of each blade and separate retracting blades 20 in order to retract skin and soft tissue and maintain the field of view. Alternatively, use of two or more retracting blades also forms an internal channel whereby other surgical instruments may be placed such that retracting blades 20 provide an open area with good visibility of the screw head to aid in the insertion of instruments and implants.

Retracting blade 20 may be a single monolithically formed unit or composed of several components connected to each other through conventional means, such as, for example, ultrasonic welding, or any other means known in the art.

Retracting blade 20 may be formed of any suitable medical grade material, including metals such as stainless steel, titanium, nickel-titanium, aluminum, or alloys thereof, or rigid or semi-rigid materials, including polymeric materials such as polyetheretherketones, polycarbonate, polypropylene, and polyethylene; and composites thereof. Retracting blade 20 may have a reflective or non-reflective coating, as appropriate to aid in increasing visibility in the wound or may have an artificial lighting feature. Retracting blade 20 may have a light emitting surface containing a light source such as a self-contained LED light engine or channel 23 for a fiber optic cable carrying light from a remote source. Retracting blade 20 may include any number of channels 23. Further, the light emitting surface may be mounted on, integrally formed with, or faceted on retracting blade 20.

Pedicle screw 30 includes threaded shaft 32 and movable head 34. Movable head 34 may be rotatable and/or have polyaxial rotation which allows for free angular movement with respect to threaded body 32. Movable head 34 includes retaining portion 35. Retaining portion 35 has channel 38. In the current embodiment, retaining portion 35 is contiguously raised from the top of movable head 34 and also contains two slots 36.

Pedicle screws are known in the art and include structure for securing a rod therein. Known securing structures include a taper lock and a set screw. Examples of such pedicle screws are disclosed in U.S. Pat. No. 5,683,392 to Richelsoph et al., U.S. Pat. No. 5,733,286 to Errico et al., U.S. Pat. No. 5,443,467 to Biedermann et al., U.S. Pat. No. 6,565,565 to Yuan et al., and published U.S. Patent Application 2007/0093817 to Barrus.

Pedicle screw 30 may be formed of any suitable medical grade material, particularly titanium. Movable head may be monolithically formed or composed of several components connected to each other through conventional means as described above.

As will be appreciated, the pedicle screw may be cannulated such that it may be translated along a gude wire, thereby facilitating insertion of the pedicle screw and the retractor device into the work site. In addition, it is contemplated that conventional insertion tools or those disclosed in U.S. patent application Ser. No. 12/104,653, filed on Apr. 17, 2008 (U.S. Patent Application Publication No. 2008/0262318), the entire contents of which are hereby incorporated by reference, may be used in conjunction with the presently disclosed retractor devices and pedicle screws.

Retracting blade 20 and pedicle screw 30 are joined by inserting projection 26 of retracting blade 20 into slot 36 of pedicle screw 30. In the current embodiment, two projections 26 are inserted into two slots 36. Passage 27 of retracting blade 20 is then aligned with channel 38 of pedicle screw 30 so that retracting blade 20 and pedicle screw 30 are releasably coupled by retention pin 40.

Retention pin 40 is used to join retracting blade 20 and pedicle screw 30. Retention pin 40 has the same or similar geometry as passage 27 of retracting blade 20 and channel 38 of screw 30 so that it may be placed therein when passage 27 is aligned with channel 38. Once joined, retracting blade 20 will move with movable head 34, as well as flex for tissue retraction. Optionally, retention pin 40 may have a tether 42, such as wire cable, for ease of removal from a remote location outside the patient.

Retractor device 10 may be constructed as shown, or in reverse so that retaining portions are on retracting blade and projections are in the pedicle screw. Further, the number, length, angle, and size of projection(s) 26 of retracting blade 20 may vary and accordingly, retaining portion 35 of pedicle screw 30 will correspond to the size, number, and configuration of projection(s) 26 so that the retracting blade 20 and pedicle screw 30 may be joined together.

Figure 3:
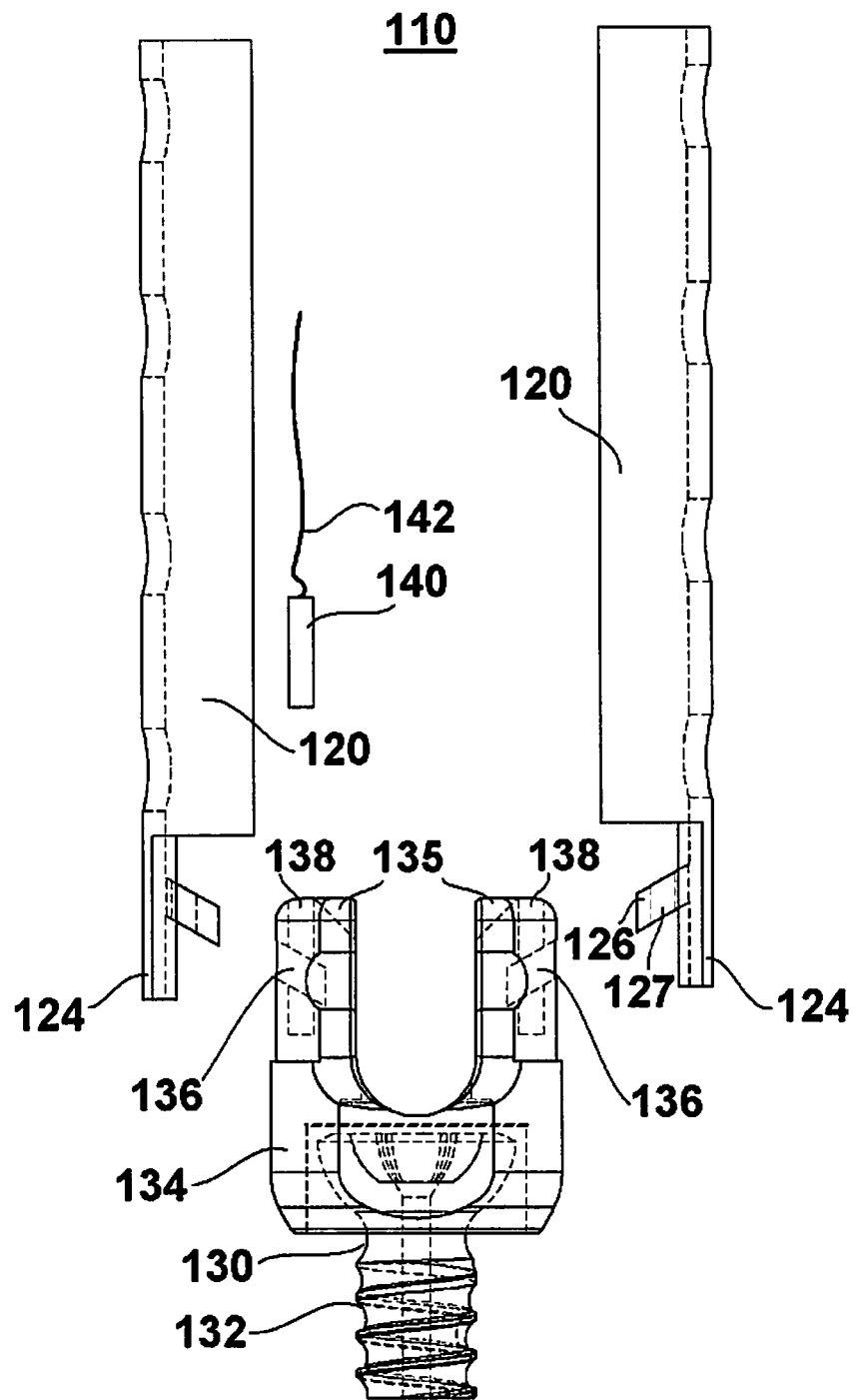
FIG. 3 is a side plan view of an alternative slot configuration of a retractor device in accordance with another embodiment of the present disclosure.

FIG. 3 illustrates another embodiment of the presently described retractor device shown generally as 110. Retractor device 110 includes retracting blade 120 and pedicle screw 130. Like components are similarly numbered as those illustrated in FIGS. 1 and 2. Pedicle screw 130 has threaded shaft 132 and movable head 134 having retaining portion 135. In this embodiment, retracting blade 120 has one projection 126 that is angled. Retaining portion 135 of pedicle screw 130 has angled slot 136.

Retracting blade 120 and pedicle screw 130 are joined by inserting angled projection 126 of the retracting blade 120 into angled slot 136 of pedicle screw 130. Passage 127 of retracting blade 120 is then aligned with channel 138 of pedicle screw 130 so that retracting blade 120 and pedicle screw 130 are releasably coupled by retention pin 140.

Retention pin 140 has the same or similar geometry as passage 127 of retracting blade 120 and channel 138 of screw 130 so that is my be placed longitudinally therein when passage 127 is aligned with channel 138 to join retracting blade 120 and pedicle screw 130. Once joined, retracting blade 120 will move with movable head 134, as well as flex thereabout with separating therefrom. Optionally, retention pin 140 may have a tether 142, such as a wire cable, for ease of removal from a remote location outside the patient.

Figure 4:
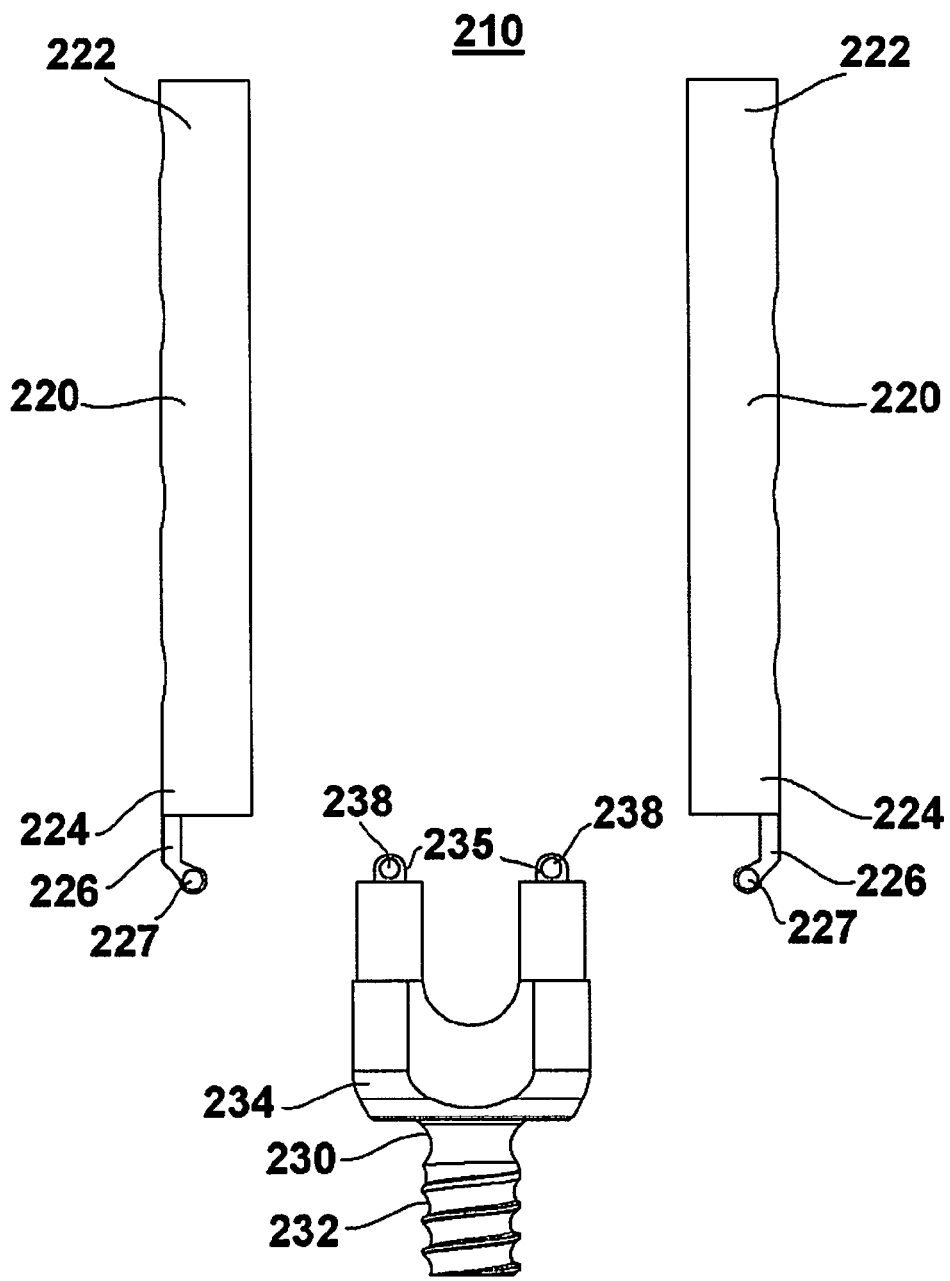
FIG. 4 is a side plan view of a retractor device with a horizontal hinge configuration in accordance with a further embodiment of the present disclosure.
Figure 5:
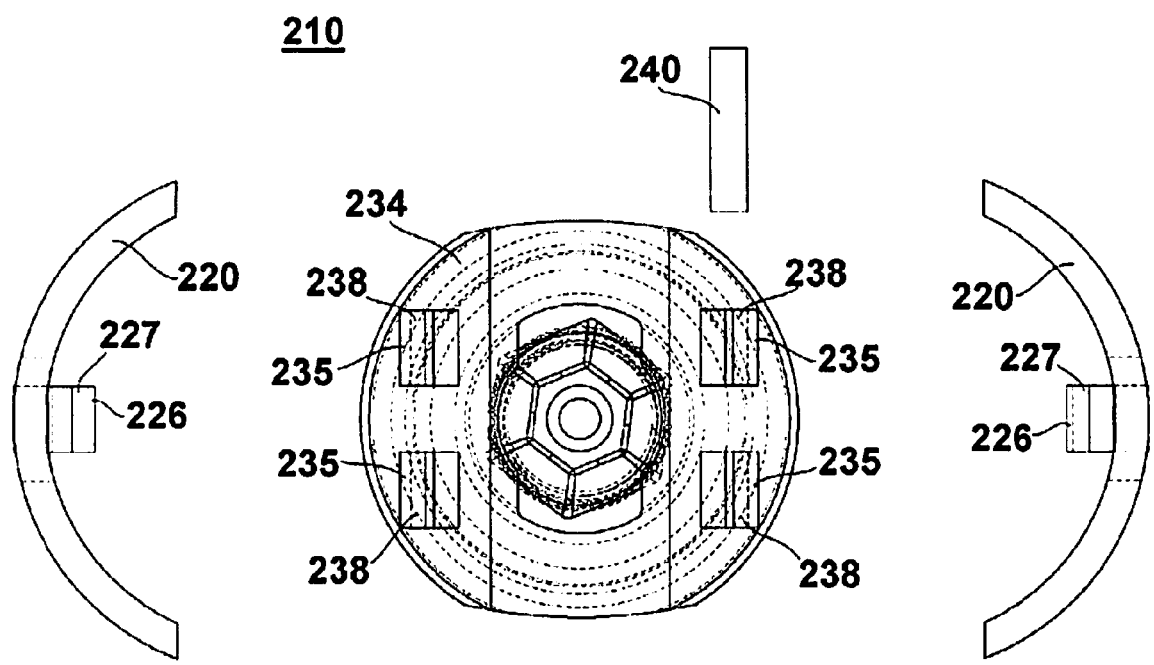
FIG. 5 is a top view of the retractor device of FIG. 4.

Referring to FIGS. 4 and 5, an alternative embodiment of the retractor device of the present disclosure is shown generally as 210. Retractor device 210 includes retracting blades 220 and pedicle screw 230. Retracting blades 220 each have proximal and distal ends 222, 224. Distal end 224 has projection 226 and slot or channel 227. Pedicle screw 230 has threaded shaft 232 and movable head 234. Movable head 234 includes at least one retaining portion 235 which has a channel 238.

In this embodiment, pedicle screw 230 has two retaining portions 235 and channels 238. Retaining portions 235 and slots 238 are joined by inserting projection 226 of retracting blade 220 between retaining portions 235 of pedicle screw 230 and securing them with retention pin 240. Retention pin 240 is transversely placed through the passage 227 of retracting blade 220 and channel 238 of pedicle screw 230 for hingedly connecting retracting blade 220 to pedicle screw 230 so that retracting blade 220 can move with movable head 234 and/or proximally thereto.

Multiple retracting blades may be used in conjunction with a single pedicle screw to allow retraction in multiple directions and multiple retracting blades may be used with multiple screws, respectively, during a single spine procedure. The retractor device may be manufactured for a single use or can be sterilized and reused.

Figure 6:
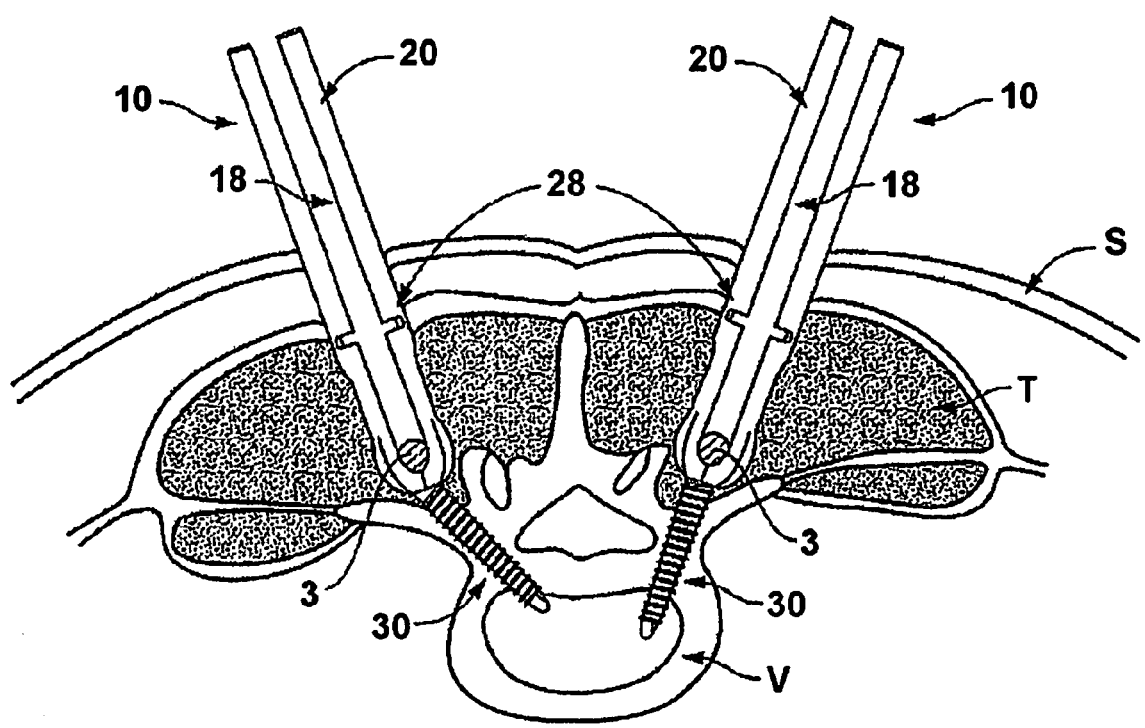
FIG. 6 is a front cross-sectional view of a vertebral body with a pair of minimally invasive retractors attached using screws with the blades in their initial position and rods positioned in the passages of the minimally invasive retractors.

A method for use of the presently disclosed system will now be described with reference to FIG. 6. Retractor device 10 is assembled with pedicle screw 30 as shown in FIG. 6. The assembled apparatus is inserted into an incision through the patient's skin S and muscle/fat tissue T such that pedicle screw 30 is subsequently threaded into a vertebral body V. Once the desired number of screws with retractor devices 10 are affixed to vertebral bodies V, retracting blades 20 are spread and/or pivoted apart to retract skin S and tissue T to create a retracted area at the target site. A rod 3 is inserted in a passage 18 when passage 18 is in an expanded state (i.e., tissue has been retracted). In a preferred method, the rod may be inserted along a path from one screw head to another, possibly subcutaneously such that it may be secured to fastening regions of pedicle screws in adjacent vertebral bodies. The retractor devices of the present disclosure are well suited for such a technique due to the unique access provided. Once the screw-rod construct is complete, retracting blades 20 are removed from the patient as described above by removing the pins holding the retracting blades to the pedicle screw. The separated portions may be moved away from the center line of the screw to provide clearance around the screw head, and then pulled out of the incision. This may be done by hand or with suitable gripping tools. An example of a retractor extracting tool is described in U.S. patent application Ser. No. 11/528,223 (referenced hereinabove).

The physician may remove retention pin 40 proximally from channel 38 using tether 42 or an elongated tool and separate retracting blades 20 from pedicle screw 30, thereby allowing proximal movement of the retracting blades 20. As such, the retracting blades 20 of the retractor device 10 are separated from pedicle screw 30 without imparting significant downward or rotational forces against the patient's body. Retracting blades 20 may then be removed from the patient and this process may be repeated for each installed retractor device 10.

As with any surgical instrument and implant, the retractors must have the ability to be sterilized using known materials and techniques. Parts may be sterile packed by the manufacturer or sterilized on site by the user. Sterile packed parts may be individually packed or packed in any desirable quantity. For example, a sterile package may contain one or a plurality of retractors in a sterile enclosure. Alternatively, such a sterile surgical kit may also include one or a plurality of bone biopsy needles(s), Jamshidi needle(s), guide wires, sterile cannulated scalpels, dilators, rods, or other surgical instruments.

The blades may be made of a light transmitting material. The retractor may include a light guide system. The light guide system has an input adapter to receive light from a light source and one or more light emitting surfaces to illuminate the surgical field.

It will be understood that various modifications may be made to the embodiments disclosed herein. Therefore, the above description should not be construed as limiting, but merely as an exemplification of the embodiments. Those skilled in the art will envision other modifications within the scope and spirit of the present disclosure. Such modifications and variations are intended to come within the scope of the following claims.

By way of example, it is contemplated that the retaining portion may be removably attached to the pedicle screw. Thus, the retaining portion could include frangible sections attached to the pedicle screw or otherwise have engagement structure for removably engaging the screw. The retractor blades could be permanently affixed to the removable retaining portion or may be separable from the removable retaining portion. In either case, the blades may be separated from the retaining portion or the retaining portion may be separated from the screw by twisting (to disengage an engagement such as a thread or bayonet mount), or by breaking off frangible sections when retraction is no longer required. It is contemplated that the retaining portion could mount to internal or external threads on upstanding portions of the pedicle screw. Such threads could be the same threads on the screw for engaging a nut or set screw to secure a rod seated in the screw.

In addition, while the foregoing description has focused on spine surgery, it is contemplated that the retractors and methods described herein may find use in other orthopedic surgery applications, such as trauma surgery. Thus, where it is desired to insert a screw or pin into bone in a minimally invasive manner, or otherwise to access a surgical target site over a guidewire, the dilator, scalpel and retractors (or some of them) of the present disclosure may be used, with or without a bone screw.

What is claimed is:

1. A retraction device comprising:
   at least one retracting blade defining a longitudinal axis and including a distal end having at least one projection and at least one passage extending through the at least one projection;
   a pedicle screw including a threaded shaft and a screw head, the screw head having at least one retaining portion and at least one channel extending through the at least one retaining portion; and
   a removable retention pin for releasably securing the retracting blade to the pedicle screw when the channel of the retaining portion is aligned with the passage of the projection, the retention pin being dimensioned to be received in the passage and the channel for hingedly connecting the retracting blade to the pedicle screw.

2. The retraction device of claim 1, wherein the passage of the projection and the channel of the retaining portion are transverse to the longitudinal axis of the retracting blade.

3. The retraction device of claim 2, wherein the pivot pin defines a pivot axis and the retracting blade is adapted to rotate about the pivot axis.

4. The retraction device of claim 1, wherein the screw head includes two retaining portions spaced to receive the projection of the retracting blade therebetween.

5. The retraction device of claim 1, wherein the retention pin is coupled to a tether.

6. The retraction device of claim 1, wherein the screw head is rotatable about the threaded shaft.

7. The retraction device of claim 1, wherein the pedicle screw is cannulated.

8. A method of performing spine surgery comprising the steps of:
   a) providing at least two retractor assemblies, each retractor assembly including at least one retracting blade hingedly attached to a pedicle screw with a retention pin, the retracting blade defining a longitudinal axis and including a distal end having at least one passage adapted to receive the retention pin, and the pedicle screw including a threaded shaft and a screw head, the screw head including a proximal end having at least one channel adapted to receive the retention pin, the retention pin releasably securing the retracting blade to the pedicle screw when the passage is aligned with the channel;
   b) securing the first pedicle screw to a portion of a first vertebral body;
   c) retracting tissue using the at least one retracting blade of the first retractor assembly;
   d) securing the second pedicle screw to a portion of a second vertebral body;
   e) retracting tissue using the at least one retracting blade of the second retractor assembly;
   f) inserting a rod between the first and second pedicle screws;
   g) securing the rod to the first and second pedicle screws; and
   h) removing the retracting blades from the pedicle screws.

9. The method of claim 8, wherein the passage of the retracting blade and the channel of the screw head of each retractor assembly are transverse to the longitudinal axis of the retracting blade, and the pivot pin defines a pivot axis, wherein the steps of retracting tissue using the at least one retracting blade of the first retractor assembly and retracting tissue using the at least one retracting blade of the second retractor assembly includes rotating the retracting blade about the pivot axis.

10. The method of claim 8, wherein the passage extends through a projection of the retracting blade, and wherein the step of providing at least two retractor assemblies includes providing a screw head including two channels, each channel disposed within a retaining portion, the retaining portions spaced to receive the projection of the retracting blade therebetween.

11. The method of claim 8, wherein the retention pin is positionable between a first position and a second position, the first position defined when the retention pin is at least partially disposed in the passage of the retracting blade and the second position defined when the retention pin is separated from the passage of the retracting blade, wherein the step of removing the retracting blades from the pedicle screws includes repositioning the retention pins from the first position to the second position.

12. A method of performing surgery comprising:
  a) percutaneously inserting a guidewire into a bony structure;
  b) inserting a cannulated bone screw with at least one pivotable and removable retracting blade coupled to the bone screw with a retention pin over the guidewire to a target site, the cannulated bone screw including a screw head having a retaining portion including a channel and the retracting blade including a projection having a passage, the retention pin releasably securing the retracting blade to the cannulated bone screw when the passage and the channel are aligned;
  c) implanting the bone screw into bone;
  d) spreading the retracting blade from a pivot point adjacent the bone screw to retract soft tissue and provide access to the target site;
  e) performing a surgical procedure at the target site; and
  f) removing the retracting blade from the bone screw.

13. The method of claim 12, wherein the passage of the projection and the channel of the retaining portion are transverse to the longitudinal axis of the retracting blade, and the pivot pin defines the pivot point, wherein the step of spreading the retracting blade includes rotating the retracting blade about the pivot pin.

14. The method of claim 9, wherein the step of removing the retracting blade from the bone screw includes separating the retention pin from at least the passage of the projection of the retracting blade.

* * * * *